(12) United States Patent
Rahn et al.

(10) Patent No.: US 6,895,268 B1
(45) Date of Patent: May 17, 2005

(54) MEDICAL WORKSTATION, IMAGING SYSTEM, AND METHOD FOR MIXING TWO IMAGES

(75) Inventors: Norbert Rahn, Forchheim (DE); Siegfried Wach, Hoechstadt (DE); Rainer Graumann, Erlangen (DE); Johannes Bieger, Erlangen (DE); Gerold Herold, Erlangen (DE); Gerd Wessels, Effeltrich (DE)

(73) Assignee: Siemens Aktiengesellschaft, Münich (DE)

( * ) Notice: Subject to any disclaimer, the term of this patent is extended or adjusted under 35 U.S.C. 154(b) by 132 days.

(21) Appl. No.: 09/605,213

(22) Filed: Jun. 28, 2000

(30) Foreign Application Priority Data

Jun. 28, 1999 (DE) .......................................... 199 29 622
Oct. 26, 1999 (DE) .......................................... 199 51 502

(51) Int. Cl.$^7$ .............................................. A61B 5/05
(52) U.S. Cl. ...................... 600/429; 606/130; 378/20; 378/205
(58) Field of Search .................... 600/407, 417, 600/420, 424, 426, 429, 431, 437, 439, 466; 606/130; 378/20, 205; 5/601

(56) References Cited

U.S. PATENT DOCUMENTS

| | | | |
|---|---|---|---|
| 5,186,174 A | | 2/1993 | Schlöndorff et al. |
| 5,638,819 A | * | 6/1997 | Manwaring et al. ........ 600/424 |
| 5,772,594 A | * | 6/1998 | Barrick ....................... 378/205 |
| 5,792,147 A | | 8/1998 | Evans et al. |
| 5,944,663 A | * | 8/1999 | Kuth et al. .................. 600/411 |
| 5,967,980 A | * | 10/1999 | Ferre et al. ................. 600/424 |
| 6,016,439 A | * | 1/2000 | Acker ......................... 600/411 |
| 6,050,724 A | * | 4/2000 | Schmitz et al. ............. 378/205 |
| 6,064,904 A | * | 5/2000 | Yanof et al. ................ 600/414 |
| 6,120,180 A | * | 9/2000 | Graumann ................... 378/206 |
| 6,149,592 A | * | 11/2000 | Yanof et al. ................ 600/427 |
| 6,216,029 B1 | * | 4/2001 | Paltieli ....................... 600/411 |
| 6,405,072 B1 | * | 6/2002 | Cosman ...................... 600/426 |
| 6,470,207 B1 | * | 10/2002 | Simon et al. ............... 600/426 |

FOREIGN PATENT DOCUMENTS

| | | |
|---|---|---|
| EP | 0 999 800 | 4/1999 |
| WO | WO98/25159 | 11/1997 |

* cited by examiner

Primary Examiner—Eleni Mantis Mercader
(74) Attorney, Agent, or Firm—Schiff Hardin LLP

(57) ABSTRACT

In a system, method and workstation, images of a first subject are acquired with an image signal acquisition unit, the position of the image signal acquisition unit is determined, the position of a second subject is determined and the position of the second subject relative to the image signal acquisition unit is also determined and an image of the second subject is mixed into an image of the first subject acquired with the image signal acquisition unit.

16 Claims, 4 Drawing Sheets

MEDICAL WORKSTATION, IMAGING SYSTEM, AND METHOD FOR MIXING TWO IMAGES

BACKGROUND OF THE INVENTION

FIELD OF THE INVENTION

The present invention is directed to a system of the type having an apparatus for acquiring images of a first subject, an apparatus for determining the position of a second subject, and the capability of mixing an image of the second subject into an image of the first subject. The invention is also directed to a medical workstation including such a system and to a method for mixing an image of the second subject into an image acquired from the first subject.

DESCRIPTION OF THE PREFERRED EMBODIMENTS

In medicine, system of the above type are utilized in clinical application fields, for example othopedics or traumatology, for supporting operative (surgical) interventions at the patient, whereby images of instruments are mixed into images of the interior of the body of the patient. This is especially advantageous when it is impossible for the surgeon to directly view the end of a medical instrument guided by the physician that has penetrated into the body of a patient. The location coordinates, i.e. the position and orientation, of the instrument in space or at an operation site are identified with a position sensor of a navigation system, the sensor being arranged at the instrument, and the image thereof is mixed into an image of the patient acquired with the image acquisition unit.

It would be desirable for the image acquired from the patient, into which the position indicator for the instrument is mixed, to the actual position and shape of a body part of the patient or an organ in the body of the patient. Since the images of the body of a patient provided for mixing instruments in during a medical intervention are usually acquired pre-operatively, i.e. before the invention, for example with a computed tomography, apparatus coincidence between a position and shape of a body part or organ shown in the image and the actual position and shape of the body part or organ during the operation is the exception. The difference usually arise because either the position of the patient in the operation on a patient support does not exactly correspond to the position of the patient during the acquisition of the image, or deformations of organs or modifications of organ position occur when opening the patient, for example due to natural movements, for example heart beat, respiration or peristalsis. An improvement in the navigation of the instrument can be achieved by registering 2D projects of the operation site during the operation, these being utilized for correcting the pre-operatively acquired images. A remaining disadvantage, however, is that the precision of mixing images of instruments in is relatively low; the surgeon, thus can only surmise the exact position of the instrument, and thus navigation represents only a rough orientation in operative interventions.

A further problem in such navigation is the mixing in itself (into pre-operatively acquired images). In order to be able to implement the mixing of an image of an instrument into a pre-operatively acquired image, it is necessary to make a spatial transformation of the coordinates in a first coordinate system for the position sensor of the navigation system, that is arranged at the instrument in a defined way, into the spatial coordinates of the image of the patient employed for the navigation and acquired with the patient image signal acquisition unit. This transformation is referred to as registration. Markers that are attached to the patient usually serves as aids for this registration. The positions of the markers are identified with the position sensor of the navigation system in the first coordinates system as well as—for example by manual entry with an input interface— in the coordinates system of the image stored in a computer acquired with the patient image signal acquisition unit and employed for navigation. A transformation ultimately can be calculated from the two point sets of the markers identified in the first coordinate system and in the coordinate system of the image employed for navigation, this transformation transforming the positions for the instrument acquired in the first coordinate system with the position sensor of the navigation system into the coordinates of the image during the navigation.

The registration, however, represents a time-consuming process that is also susceptible to error. Moreover, the manipulation and the identification of the markers in the pre-operative surroundings often proves problematical.

SUMMARY OF THE INVENTION

An object of the present invention is to provide a system of the type initially described wherein the mixing of the image of a second subject into an image of a first subject acquired with a patient image acquisition apparatus is simplified. A further object of the invention is to provide a method for simplified mixing of an image of a second subject into an image acquired from a first subject.

The first object is inventively achieved in a system having an image signal acquisition unit for acquiring images of a first subject, an arrangement for determining the position of the image signal acquisition unit, an arrangement for determining the position of a second subject, a unit for determining the position of the second subject relative to the image signal acquisition unit, a mixing unit for mixing an image of the second subject into an image of the first subject acquired with the image signal acquisition unit. The invention thus allows the positions and orientations of the image data acquired with the image signal acquisition unit to be known relative to that apparatus on the basis of unambiguous, spatial relationships or allow those positions and orientations to be identified or determined in a simple way. Due to the determination of the position of the image signal acquisition unit in reference coordinate system, the position and orientation of an image coordinate system capable of describing an image acquired with the image signal acquisition unit is defined or can be determined with respect to the reference coordinate system in a simple way. Since, according to the invention, the position of the second subject also can be determined in the reference coordinate system, an image of the second subject given introduction of the second subject into the image acquisition region of the image signal acquisition unit or given introduction of the second subject into the region of the image data acquired with the image signal acquisition unit, can be mixed into the image acquired with the image signal acquisition unit in a simple way without implementation of a time-consuming registration that is susceptible to error.

The arrangement for determining the position of the image signal acquisition unit, the arrangement for determining the position of the second subject and the arrangement for determining the position of the second subject relative to the image signal acquisition unit can be implemented differently from one another and can operate, for example, on the basis of signal-carrying waves. The first arrangement determines the position of the image signal acquisition unit in a first coordinate system and the second arrangement determines the position of the second subject in a second coordinate system. The arrangement for determining the position of the second subject relative to the image signal acquisition unit indicates the position of the first and second arrangement relative to a reference coordinate system, so that the positions of the image signal acquisition unit and of the second subject are known in the reference coordinate system. The mixing of the image of the second subject into an image of the first subject acquired with the image signal acquisition unit thus is unproblematic due to the known positions and orientations of the image data acquired with the image signal acquisition unit in the reference coordinate system.

In a preferred embodiment of the invention, the overall system employs a navigation system that identifies the position of the signal acquisition unit as well as the position of the second subject as well as the position of the second subject relative to the image signal acquisition unit. In a version of this embodiment, the navigation system includes detectable marks and/or position sensors that can be attached to a subject. Such marks can, for example, be marks that are optically detectable with a camera system. The position sensors can be fashioned as transmitters whose signal are received by a receiver of the navigation system and all correspondingly interpreted for determining the respective positions of the position sensors. The position sensors alternatively can be fashioned such that their positions are detectable by the navigation system within an electromagnetic field emitted by a transmitter. The determination of the position usually ensues with a navigation computer of the navigation system. As a result of the suitable attachment of such marks and/or position sensors at the image signal acquisition unit at the second subject, the respective positions of the image signal acquisition unit and the second subject as well as their relative position with respect to one another in the reference coordinate system can be determined in a simple way with a signal navigation system. Optical navigation systems as distributed, for example, by the Radionix Company as well as electromagnetic navigation systems as distributed, for example, by the Ascension Company are suited as suitable navigation systems for determining the respective positions of the image signal acquisition unit and the second subject as well as their relative position with respect to one another.

In further versions of the invention, the image signal acquisition unit is at least one ultrasound sensor connectable to an ultrasound device and/or an X-ray system arranged at an X-ray apparatus and including an X-ray source and an X-ray receiver. The X-ray apparatus is preferably a portable C-arm X-ray apparatus whose C-arm is isocentrically adjustable. The position of the isocenter, in which a subject to be examined is usually placed in X-ray examinations, is likewise known in the reference coordinate system due to the determination of the position of the C-arm in the reference coordinate system, so that the positions and orientations of the image data acquired with the X-ray system arranged at the C-arm are known in the reference coordinate system.

In a further version of the invention, 3D images of the subject can be produced with the image signal acquisition unit. When, for example, the inventive system is a medical system, 3D images of a body part or of an organ of a patient can be intra-operatively produced with images signal acquisition unit so that the pre-conditions for an exact mixing of an image of an instrument into one of the 3D images are created. The mixing thereby corresponds with high coincidence to the real position and orientation of the instrument relative to the body of the patient. The exact determination of the position and orientation of the image signal acquisition unit and of the instrument preferably ensues with the assistance of the navigation system, and the corresponding mixing of the image into a generated 3D image ensues with the assistance of the mixing unit, which, for example, can be an image computer or the navigation computer in practice. Due to the excellent agreement with the real conditions prevailing at the operation site, such mixing of an image of an instrument into a 3D image showing the actual position and shape of a body part or organ represents effective and dependable support for a surgeon in operative interventions. This is especially true when the surgeon has no view of the end of the instrument, for example because the instrument has penetrated tissue. As used herein "mixing in" an image of a subject or instrument does not necessarily require a true-to-life "picture" of the subject or of the instrument. The mixed in image can be only schematic, as long as at least that part of the subject or of the instrument relevant for the navigation can be recognized.

In another embodiment of the invention 2D images of the first subject can be produced in real time with the image signal acquisition unit. 2D imaging in real time, for example, is required in the medical navigation given interventions at moving anatomical regions. An ultrasound probe can be used to produce such 2D, but it is to be expected that the instrument to be mixed into the 2D ultrasound image usually will not be permanently located in the image plane of the ultrasound fan emitted by the ultrasound probe due to relative movements between the ultrasound probe and the body of the patient and the instrument to be navigated. Therefore, the image of the instrument—in a version of the invention—is mixed projectively and the distance thereof from the image plane of the ultrasound fan is mixed into a generated 2D ultrasound image on the basis of the known position of the image plane of the ultrasound fan and the position of the instrument in the reference coordinate system, for supporting a surgeon carrying out the invention.

In another embodiment of the invention the position of the image signal acquisition unit, i.e. the location and orientation thereof, can be acquired simultaneously with the position of the second subject to be mixed into the image acquired with the image signal acquisition unit. In a version of this embodiment, the system also has an acceptance device for the first subject and an arrangement for determining the position of the acceptance device, whereby the position of the acceptance device can be acquired simultaneously with the respective positions of the image signal acquisition unit and the second subject. For medical applications, such an acceptance device is, for example, a patient support on which the patient is positioned during an operative intervention. The determination of the positions of the image signal acquisition unit, the instrument, and the acceptance device preferably ensues with the navigation system. In this way, the position and orientation of the instrument always can be calculated online due to the simultaneous acquisition of the positions of the image signal acquisition unit, the instrument, and the patient support, even given adjustment motions of the acceptance device relative to the instrument and to the image signal acquisition unit. The position and orientation of the instrument thus can be mixed, in conformity with the situation, into an image of the patient acquired with the image signal acquisition unit. With this system, thus, images of a first subject, provided with images of a second subject into considerations that take changes in the position of the second subject, changes in the position of the image signal acquisition unit and/or changes in the position of the acceptance device, can be generated online. The images also can be continuously generated.

The aforementioned object is also achieved in a medical workstation that includes an embodiment of the inventive system.

The workstation can be of a type for minimally invasive interventions and/or the images of the first subject can be intra-operatively produced, so that the navigation of medical instruments relative to the body of a patient can be exactly implemented.

The second object of the invention is achieved in a method for mixing an image of a second subject into an image acquired from a first subject that includes the steps acquiring an image of a first subject with an image signal acquisition unit, determining the position of the image signal acquisition unit, determining the position of a second subject, determining the position of the second subject relative to the image signal acquisition unit, and mixing an image of the second subject into the image of the first subject acquired with the image signal acquisition unit.

In the inventive method an image signal acquisition unit can be used wherein the positions and orientations of the image data acquired therewith are known on the basis of unambiguous spatial relationships, or can be determined or identified in a simple way. After the determination of an image dataset and the identification of the position and orientation thereof in a reference coordinate system, the image of the second subject can also be mixed into an image of the first subject produced from the image dataset by determining the position of the second subject in the reference coordinate system. Insofar as the second subject is not located in the image region of the first subject, there is also the possibility of projectively mixing an image of the second subject into the image of the first subject. In any case, the mixing of an image of the second subject into an image of the first subject acquired with the image signal acquisition unit can ensue without the implementation of a time-consuming registration that is susceptible to error.

DESCRIPTION OF THE PREFERRED EMBODIMENTS

The inventive system is described below with reference to the example of a medical system that is utilized at a medical workstation for minimally invasive interventions.

Figure 1:
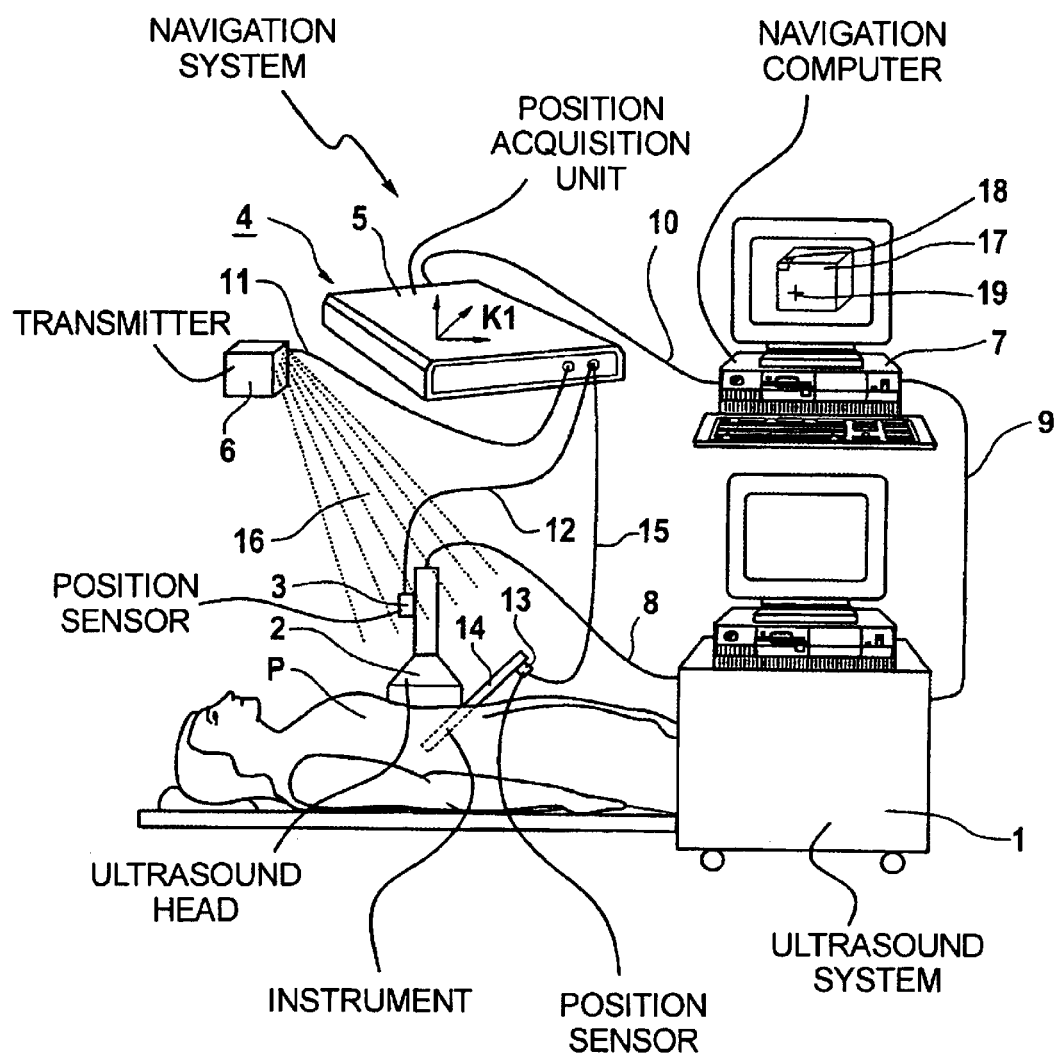
FIG. 1 shows an inventive system provided for medical navigation having an ultrasound system with an extracorporeally arranged ultrasound sensor.

In the exemplary embodiment shown is FIG. 1, the image signal acquisition unit is an ultrasound (probe) head 2 that can be applied to the body surface of a patient P and that is connected with a line 8 to a known ultrasound 1 having an image processing unit and a display. 2D images from the interior of the body of the patient P can be acquired with the ultrasound head 2 in a known way in sector scans and can be displayed on the display of the ultrasound system 1 in a way that is not shown.

The workstation also has navigation system 4 that includes a position acquisition unit 5, a transmitter 6, a navigation computer 7, which can be standard PC, and position sensors 3 and 13 that can be attached to subjects. Thus ultrasound system 1 is connected via a line 9 to the navigation computer 7, the navigation computer 7 is connected via a line 10 to the position acquisition unit 5 and the latter is connected via a line 11 to the transmitter 6 and via lines 12 and 15 to the position sensors 3, 13.

In the examplary embodiment, the position sensor 3 of the navigation system 4 is arranged at the ultrasound head 4 in such a defined way so that not only the position of the ultrasound transmitter and receiver surfaces of the ultrasound head 2, but also the position, i.e. the attitudes and orientations, of the image data acquired with the ultrasound head 2, are able to be known in a reference coordinate system K1 due to the determination of the position of the position sensor 3 in the reference coordination system K1 defined by the position acquisition unit 5. The position sensor 13 is arranged at a surgical instrument 14 in a defined way so that, by determining the position of the position sensor 13, the position of the tip of the instrument 14 also is known, the latter having partly penetrated into the of the patient P and being no longer visible in the exemplary embodiment shown in FIG. 1. The transmitter 6 of the navigation system 4, which emits electromagnetic waves in the exemplary embodiment, is likewise arranged in the reference coordinate system K1 of the position acquisition unit 5 in a defined way.

During operation of the system, the transmitter 6 generates an electromagnetic field 16 (indicated with broken line) in which the position sensors 1 and 13 secured to the ultrasound head 2 and the surgical instrument 14 are arranged. On the basis of the signals generated by the position sensors 3 and 13 and transmitted to the position acquisition unit 5 via the lines 12 and 15, the position acquisition unit 5 can determined the position, i.e. the attitudes and orientations, of the ultrasound head 2 and the surgical instrument 14 relative to the reference coordinate system K1.

A 3D ultrasound image dataset 17 can also be generated with the navigation computer 7 from the 2D ultrasound images acquired with the ultrasound head 2 of the ultrasound apparatus 1, whereby the positions of the ultrasound head 2 in every exposure of a 2D ultrasound image are known due to the position acquisition by the position acquisition unit 5. Due to the known spatial relationship between the acquired 2D ultrasound image data and the transmission and reception surfaces of the ultrasound head 2, the attitude and orientation in the reference coordinate system K1 are thereby known for each image datum of the generated 3D ultrasound image dataset 17 (shown schematically as a cube in FIG. 1) from which various 3D images of the inside of the patient P can be reconstructed. Accordingly, the attitude and orientation in the reference coordinate system K1, as well as the voxel size, for example in millimeters and degrees, are also known in the reference coordinate system K1 for an arbitrary 3D image cube 18 reconstructed from the 3D ultrasound image dataset. Since the position, i.e. the attitude and orientation, of the instrument 14 in the reference coordinate system K1 also is known due to the position acquisition by the position acquisition unit 5, an image of the instrument 14 can be unambiguously mixed into a generated image of the patient P for each position determined by the position acquisition system 5, as long as the position sensors 3, 13 of the navigation system 4 are situated in the electromagnetic field generated by the transmitter 6 and insofar as the instrument 14 is situated in the region of the relevant image. In a schematic illustration in FIG. 1, the tip of the surgical instrument 14 in the form of a cross 19 is mixed into the 3D ultrasound image dataset 17 from the interior of the body of the patient P that was generated from the 2D ultrasound images acquired with the ultrasound head 2.

In the way described above, thus, an image of any desired surgical instrument equipped with a position sensor can be mixed into a 3D ultrasound image intra-registration operatively generated during a surgical intervention at a patient. Inventively, no registration is required for mixing in the instrument.

The instrument 14 in the exemplary embodiment shown in FIG. 1 is rigid instrument, for example a forceps, an HF scalpel, scissors, a biopsy needle or puncture needle, for which reason the position sensor 13 can be extracorporeally arranged. The position of the tip of the instrument 14 to be visualized, namely the position thereof in the reference coordinate system K1, thus can be determined as already describe with a transformation of the coordinates of the position sensor 13 into the coordinates that correspond to the tip of the instrument 14.

Figure 2:
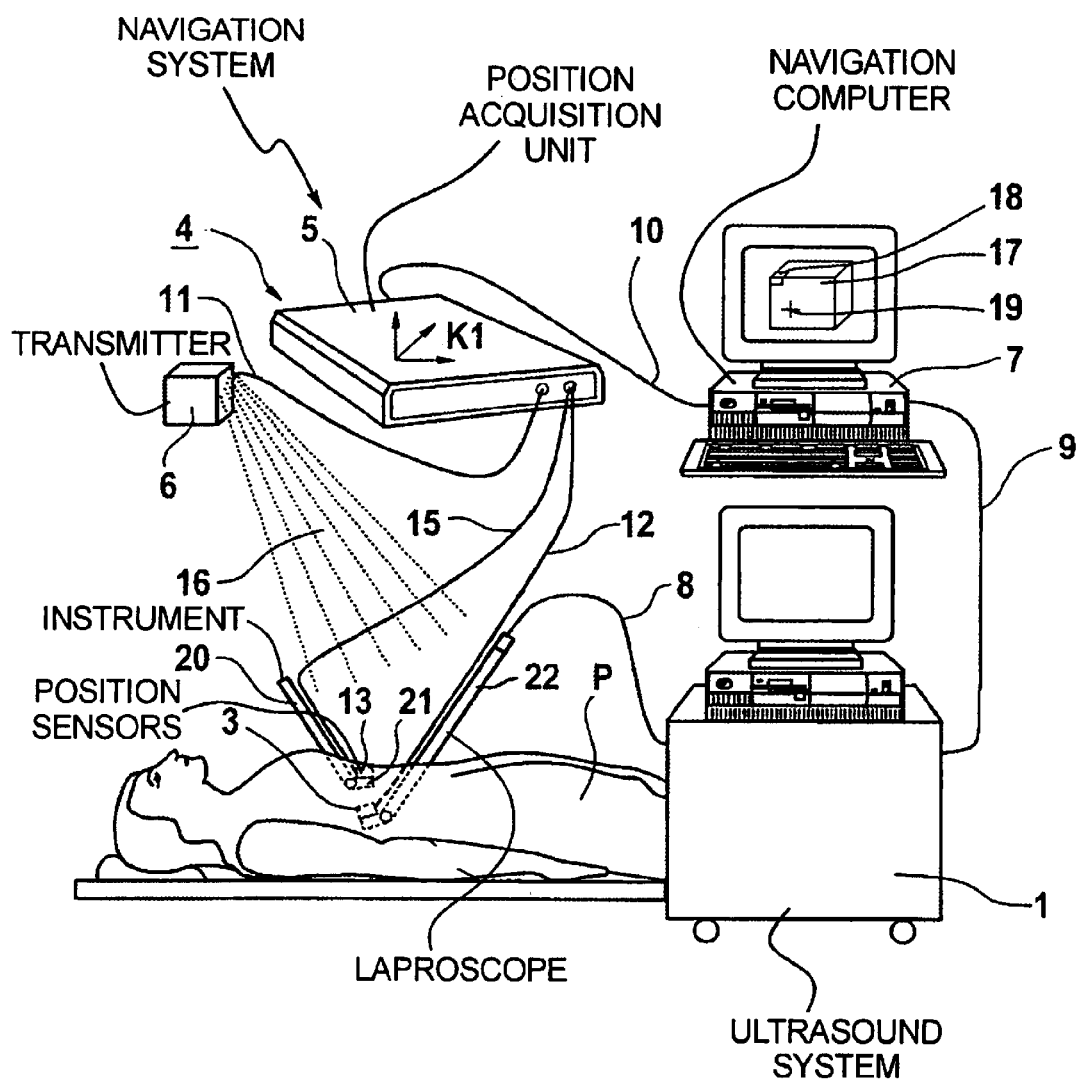
FIG. 2 shows an inventive system provided for medical navigation having an ultrasound system with an ultrasound laparoscope.

FIG. 2 shows an exemplary embodiment of the invention wherein an instrument 20 with a flexible instrument part, a flexible tip 21 in the exemplary embodiment, is employed. In order to be able to exactly mix the position of the tip 21 into an image reconstructed from the 3D ultrasound image dataset 17, the position sensor 13 is located at the tip 21 of the instrument 20. Such an instrument 20 having a flexible part can, for example, be an endoscope, a catheter or other instruments that can be angled.

Differing from the exemplary embodiment described in FIG. 1, the acquisition of the 2D ultrasound images required for generating the 3D ultrasound image dataset 17 also ensues with an intracorporeal ultrasound sensor, known as an ultrasound laparoscope 22. Since the ultrasound laparoscope 22 is likewise flexible, the position sensor 3 is integrated in the tip of the ultrasound laparoscope 22, in a defined way relative to the ultrasound transmission and reception surfaces. As in the previously described exemplary embodiment, 2D ultrasound images can be generated with the ultrasound laparoscope 22 from which the navigation computer 7 can generate the 3D ultrasound image dataset 17 on the basis of the position of the ultrasound laparoscope 22, identifiable for each 2D ultrasound image. As in the exemplary embodiment shown in FIG. 1, the position in the reference coordinate system K1 is known for each image datum of the generated 3D ultrasound image dataset 17 in the exemplary embodiment shown in FIG. 2, due to the known spatial relationship between the acquired ultrasound data and the ultrasound transmission and reception surfaces of the ultrasound laparoscope 22. Accordingly, the attitude and orientation of a 3D image cube 18 in the reference coordinate system K1, arbitrarily reconstructed form the 3D ultrasound image data set 17, as well as the voxel size, for example in millimeters the degrees, are also known. Since the position of the tip 21 of the instrument 20 is also known due to the position acquisition with the position acquisition unit 5, the tip 21 of the instrument 20 can be mixed into the 3D ultrasound image dataset 17 generated with the ultrasound laparoscope 22, or into a 3D image cube 18, as in the case of the previously exemplary embodiment. The mixing of the image of the tip 21 of the instrument 20 into the 3D ultrasound image dataset 17 is schematically shown with a cross 19 in FIG. 2.

Figure 3:
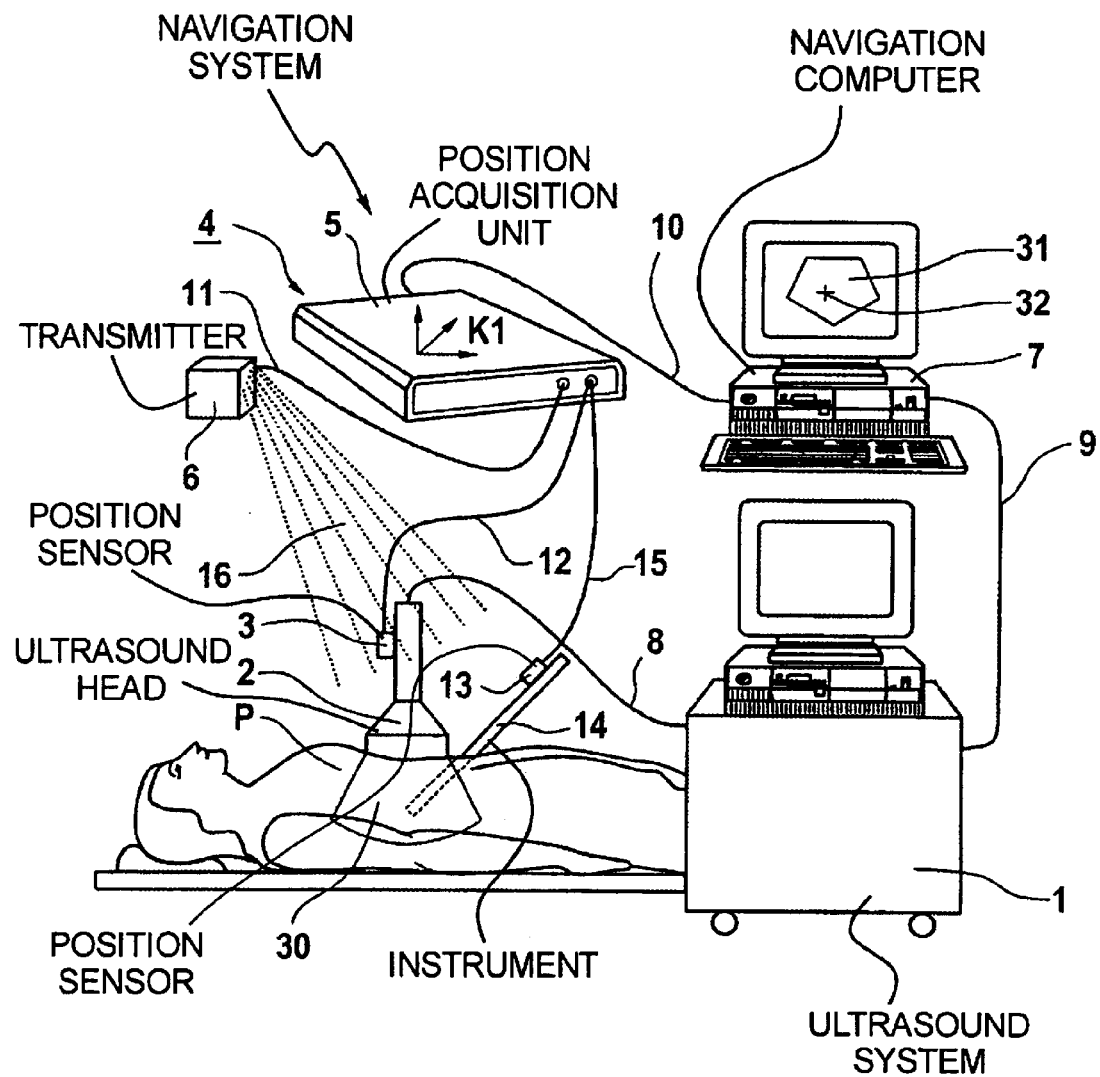
FIG. 3 shows an inventive system provided for medical navigation having an ultrasound system with an extracorporeally arranged ultrasound sensor for producing 2D images in real time.

FIG. 3 illustrates the navigation with 2D imaging in real time on the basis of ultrasound images acquired in real time. The arrangement shown in FIG. 3 essentially corresponds to the arrangement of the inventive system shown in FIG. 1, so that the components shown in FIG. 3 that are identical to components of the exemplary embodiment shown in FIG. 1 are provided with the same reference characters.

In a known way, a sector 30 can be scanned with ultrasound head 2 applied to the body surface of the patient P, this being displayable on a viewing means of the navigation computer 7 as sector scan 31. The attitude and orientation of the sector scan 31 is known due to the position acquisition with the position acquisition unit 5 and due to the known relationship between the acquired 2D ultrasound data and the transmission and reception surfaces of the ultrasound head 2 in the reference coordinate system K1. With the assistance of the position sensor 13, the position of the instrument 14 can be simultaneously determined in the reference coordinate system K1 with the position acquisition unit 5 and, accordingly, the image of the instrument 14 can be correspondingly mixed into sector scan 31 visualized in the navigation computer 7 and displayable on a viewing means. In the present exemplary embodiment, the position of the tip of the instrument 14 is mixed into the sector scan 31 in the form of a cross 32.

As a result of the acquisition of the images in real time, the visualization of the instrument 14 in the sector scan 31 could also be achieved without acquiring the position of the instrument 14 if the instrument 14 were always situated in the image plane of the sector 30. This, however, usually cannot be expected due to the manual positioning of the ultrasound head 2. Due to the position acquisition of the position sensor 3 arranged at the ultrasound head as well as of the position sensor 13 arranged at the instrument, however, the attitude of the instrument 14 relative to the sector 30 is known, so that the tip of the instrument 14 also can be projectively mixed into the sector scan 31 even if the tip of the instrument 14 or the entire instrument 14 were not visible in the sector scan 31. Inventively, the spacing of the tip of the instrument 14 from the sector 30 is mixed in, for example as an orientation aid for the surgeon undertaking the intervention, given this projective mixing of the tip of the instrument 14 into the sector scan 31. Specifying the spacing for a user can ensue, for example, by means of a circle whose diameter corresponds to the spacing between the instrument 14 and the sector 30 or using color codings, whereby the color intensities indicate the spacing between the instrument 14 and the sector 30. For example, a surgeon can be assisted in the guidance of the ultrasound head 2, whereby, since the attitudes and orientations of the ultrasound head 2 and of the surgical instrument 14 are available in the navigation computer 7, possibilities for positioning the ultrasound head 2, for example with reference to the inclination or the rotation of the ultrasound head 2 on the body surface, can be display in order to make the instrument 14 visible in the sensor scan 31.

Figure 4:
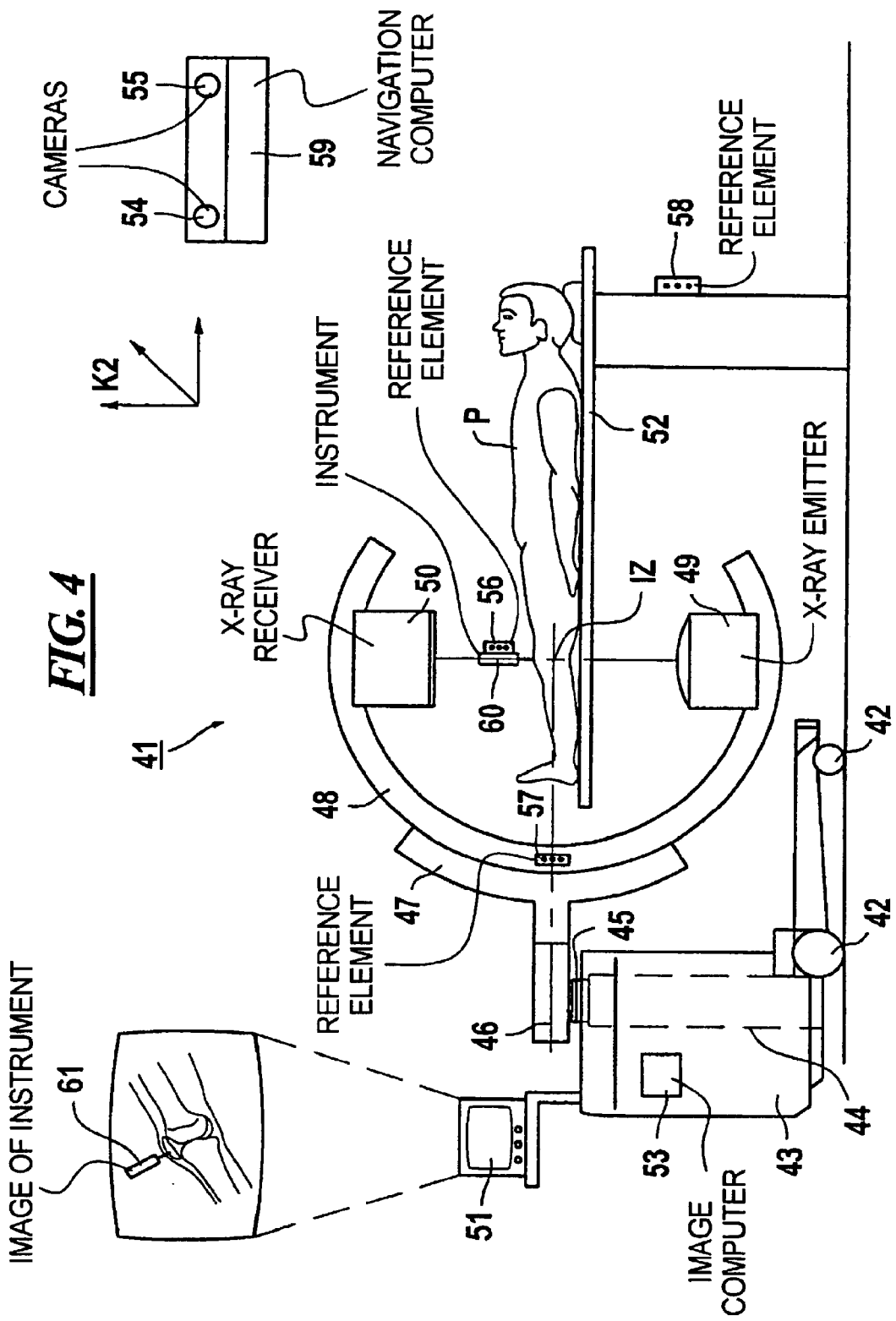
FIG. 4 shows an inventive system provided for medical navigation having a C-arm X-ray apparatus.

FIG. 4 shows a further exemplary embodiment of an inventive system provided for medical navigation, having a C-arm X-ray apparatus 41 with an apparatus cart 43 movable on wheels 42. The C-arm X-ray apparatus 41 has a lifting mechanism (only schematically indicating in FIG. 4) with a column 45. A holder 46 is connected to a holding mechanism 47 for a C-arm 48 having an isocenter IZ. An X-ray emitter 49 and an X-ray receiver 50 are arranged at the C-arm opposite one another. In the exemplary embodiment, the X-ray receiver 50 is known solid state detector. The X-ray receiver 50, however, can be an X-ray image intensifier, but a solid state detector has the advantage over an X-ray image intensifier of supplying geometrically undistorted X-ray images. The X-ray images acquired with the receiver 50 can be displayed on a display 51 in a known way.

The C-arm X-ray apparatus 41 shown in FIG. 4 allows a 3D image dataset of the body or of body parts of a patient P borne on a vertically and horizontally adjustable patient support 52 to be produced therewith, with various 3D images of the body of the patient being reconstructable therefrom. For 3D imaging, an image computer 53 that is arranged in the apparatus cart 43 of the C-arm X-ray apparatus 41, and that is connected in a way not shown to the receiver 50 and the display 51 is provided in the exemplary embodiment. In a known way in the image computer 53 uses 2D projections to reconstruct 3D images of a body part to be presented. These 2D projections are acquired given an adjustment of the C-arm 48, for example along its circumference, around a body part of the patient P placed in the isocenter IZ of the C-arm 48.

Using a navigation system that is an optical navigation system in the exemplary embodiment, an image of an instrument employed by a surgeon (not shown in FIG. 4) can be mixed into 3D images of the body of the patient P produced during the operation. As in the case of the 3D images acquired with ultrasound, the surgeon is provided with effective and dependable support in the operative intervention. In order, however, to be able to exactly position an instrument on the basis of the image information, exact images of the real operation site that are obtained by the acquisition of 3D images during the operation are required.

In the exemplary embodiment shown in FIG. 4, the navigation system has cameras 54, 55 and reference elements 56 through 58 detectable with the cameras 54, 55 that are arranged at instruments or subjects to be identified as to their position and that are acquired by the cameras 54, 55. A navigation computer 59 of the navigation system interprets the pictures acquired with the cameras 54, 55 and can determine the positions, i.e. the attitudes and orientations, of the reference elements 56 through 58, and thus of the instruments or subjects, with respect to a reference coordinate system K2 on the basis of the acquired reference elements 56 through 58.

In the exemplary embodiment, the reference element 56 is arranged at a surgical instrument, the reference element 57 is arranged at the C-arm 48 of the C-arm X-ray apparatus 42 and the reference element 58 is arranged at the patient support 52. In this way, the navigation computer 59 can respectively determine the current positions of the C-arm 48 and thus of the isocenter IZ of the C-arm 48, and the respective position of the instrument 60 and the patient support 52 on the basis of the acquired camera pictures. The navigation computer 59, which is connected to the image computer 53 in a way that is not shown, makes the data about the current positions of the isocenter IZ, the instrument 60 and the patient support 52 available to the image computer 53. On the basis of the position information, the image computer 53 can mix an image of the instrument 60 into a 3D image acquired with the C-arm X-ray apparatus 41 during the operation, whereby the attitudes and orientation of the generated image dataset in the reference coordinate system K2 are known on the basis of the known position of the isocenter IZ. Inventively, no registration is thereby required for mixing in the image of the instrument 60. Such a mixing of an image 61 of the instrument 60 into a generated 3D image is shown as an example in FIG. 4.

Since the movements of the instrument 60, of the C-arm 48 and the patient support 52 are simultaneously and continuously acquired via the cameras 54, 55 and the computer 59, the mixing of the image of the instrument 60 into a 3D image acquired with the C-arm X-ray apparatus 41 can be adapted online corresponding to the modified situation. Not only static but also continuously successive 3D images provided with the mixed-in image of the instrument 60 can be generated in this way.

The positions of the instrument, the image signal acquisition unit, and the patient support, moreover, need not be simultaneously acquired. A nearly simultaneous acquisition, however, is required when the image of the instrument is to be mixed online into generated 3D images or into 2D images acquired in real time, particularly following changes in the positions of the instrument or of the patient support.

Moreover, the workstations shown in FIGS. 1 through 3 can also have a patient support whose positions are acquired simultaneously with the respective positions of the instrument and the image signal acquisition unit.

The determination of the respective positions of the image signal acquisition unit, the instrument, and the patient support need not necessarily ensue with a navigation system. These positions alternatively can be determined and placed into relationship with one another by some other suitable arrangement for position acquisition that, for example, operates on the basis of signal-carrying waves.

An optical navigation system instead of a navigation system operating on the basis of electromagnetic fields can be utilized in the exemplary embodiments described in FIGS. 1 through 3, and a navigation system operating on the basis of electromagnetic waves can be utilized in the exemplary embodiment described in FIG. 4 instead of the optical navigation system.

The inventive system has been described above with regard to the example of a medical system for the navigation of medical instruments. The system, however, is not limited to use in medicine.

Any system wherein the attitudes and orientation of the acquired image data in the reference coordinate system are known due to the knowledge of the position of the image signal acquisition unit can be utilized as the image signal acquisition unit.

Although modifications and changes may be suggested by those skilled in the art, it is the intention of the inventors to embody within the patent warranted hereon all changes and modifications as reasonably and properly come within the scope of their contribution to the art.

We claim as our invention:

1. A system comprising:
   an image signal acquisition unit for acquiring 2D image signals of an examination subject in real time, and an imaging unit for producing a 2D image of the examination subject in an image plane from said 2D image signals;
   an instrument having a tip adapted for interaction with the examination subject;
   a navigation system including a position acquisition unit for determining a position of said image signal acquisition unit and for determining a position of said tip relative to said position acquisition unit; and
   a mixing unit connected to said imaging unit for mixing a representation of said tip into said 2D image and, if said tip is not located in said image plane, for determining a distance of said tip from said image plane and for mixing a designation of said distance into said 2D image, said designation being alterable and indicating a magnitude of said distance.

2. A system as claimed in claim 1 wherein said navigation system includes identifiers, selected from the group consisting of detectable marks and position sensors, which are respectively attachable to said image signal acquisition unit and to said second subject and which are identifiable as to position by said position acquisition unit.

3. A system as claimed in claim 1 wherein said image signal acquisition unit comprises an ultrasound laparoscope.

4. A system as claimed in claim 1 wherein said image signal acquisition unit comprises an X-ray source and an X-ray receiver.

5. A system as claimed in claim 1 wherein said imaging unit produces a 3D image of said first subject from said image signals.

6. A system as claimed in claim 1 wherein said position acquisition unit simultaneously identifies the position of said image signal acquisition unit and the position of said second subject.

7. A system as claimed in claim 1 further comprising an acceptance device for said first subject and wherein said position acquisition device identifies a position of said acceptance device simultaneously with identifying the position of said image signal acquisition unit and the position of said second subject.

8. A system as claimed in claim 1 wherein, if said tip is not located in said image plane, said mixing unit mixes a projection of said tip in said image plane into said 2D image.

9. A system as claimed in claim 1 wherein said mixing unit mixes a circle, as said designation, into said 2D image, said circle having a diameter which is alterable dependent on said magnitude of said distance.

10. A system as claimed in claim 1 wherein said mixing unit mixes said designation into said 2D image with an alterable color intensity indicating said magnitude of said distance.

11. A system comprising:

a C-arm X-ray image data acquisition unit for acquiring 3D image data of a patient, and an image unit for producing a 3D image of the patient from said image data;

a support mechanism for support the first subject;

a position acquisition system for determining a position of said C-arm X-ray image data acquisition unit, said support mechanism, and a medical instrument adapted for insertion into the patient, relative to said C-arm X-ray image data acquisition unit; and a mixing unit for mixing a representation of the medical instrument into said 3D image of said patient dependent on said position of said C-arm X-ray image data acquisition unit, said support mechanism, and said medical instrument relative to said C-arm X-ray image data acquisition unit.

12. A system as claimed in claim 11 wherein said imaging unit produces a 2D image of said first subject from image signals.

13. A system as claimed in claim 12 wherein said 2D image represents an image plane in said first subject, and wherein said mixing unit mixes an indication of a distance of said second subject from said image plane into said 2D image.

14. A system as claimed in claim 11 wherein said navigation system includes identifiers, selected from the group consisting of detectable marks and position sensors, which are respectively attachable to said C-arm X-ray image data acquisition unit and to said second subject and which are identifiable as to position by said position acquisition unit.

15. A system as claimed in claim 11 wherein said position acquisition unit simultaneously identifies the position of said C-arm X-ray image data acquisition unit and the position of said medical instrument.

16. A system as claimed in claim 11 wherein said position acquisition unit simultaneously determines said position of said C-arm X-ray image data acquisition unit, said support mechanism and said medical instrument relative to said C-arm X-ray data acquisition unit.

* * * * *